(12) United States Patent
Lipps

(10) Patent No.: US 7,129,334 B2
(45) Date of Patent: Oct. 31, 2006

(54) SYNTHETIC PEPTIDE AND USES FOR SAME

(76) Inventor: Binie V. Lipps, 4509 Mimosa Dr., Bellaire, TX (US) 77401

( * ) Notice: Subject to any disclaimer, the term of this patent is extended or adjusted under 35 U.S.C. 154(b) by 198 days.

(21) Appl. No.: 10/466,193

(22) PCT Filed: Jan. 30, 2002

(86) PCT No.: PCT/US02/02633

§ 371 (c)(1),
(2), (4) Date: Jul. 15, 2003

(87) PCT Pub. No.: WO02/061044

PCT Pub. Date: Aug. 8, 2002

(65) Prior Publication Data
US 2004/0058874 A1 Mar. 25, 2004

Related U.S. Application Data

(60) Provisional application No. 60/264,984, filed on Jan. 30, 2001.

(51) Int. Cl.
A61K 38/22 (2006.01)
C12P 21/00 (2006.01)
(52) U.S. Cl. .................. 530/399; 530/300; 514/2; 514/8; 424/278.1
(58) Field of Classification Search ............ 530/399, 530/300; 514/2, 8; 424/278.1
See application file for complete search history.

(56) References Cited

U.S. PATENT DOCUMENTS

| 3,865,689 | A | * | 2/1975 | Goldenberg | ............... 435/70.3 |
| 5,891,432 | A | * | 4/1999 | Hoo | ........................ 424/93.21 |
| 6,307,031 | B1 | | 10/2001 | Lipps | |
| 6,316,602 | B1 | | 11/2001 | Lipps | |
| 6,500,933 | B1 | * | 12/2002 | Margolin et al. | ............ 530/395 |
| 2004/0214184 | A1 | * | 10/2004 | Skubitz et al. | ................. 435/6 |

OTHER PUBLICATIONS

Nagel et al. (1993) Genomic organization, splice variants and expression of CGM1, a CD66-related member of the carcinoembryonic antigen gene family. Eur. J. Biochem. vol. 214, No. 1, pp. 27-35.*

* cited by examiner

Primary Examiner—Jon Weber
Assistant Examiner—Samuel Wei Liu
(74) Attorney, Agent, or Firm—John R. Casperson

(57) ABSTRACT

Beta taipoxin obtained the taipoxin component of the venom of the taipan snake, *Oxyuranus s. scutellatus*, was fragmented by trypsin digestion. The fragment which showed the highest activity on skin cells for mitogenic activity and on PC12 cells for neurite growth was named Oxynor peptide. This fragment consisted of 21 amino acids and had the sequence from the N-terminal: Lys Gly Gly Ser Leu Leu Asn Phe Ala Asn Leu Ile Glu Asn Asp Val Pro Ile Asp His Met. Synthetic Oxynor peptide was constructed using ten amino acids (Ser Leu Leu Asn Phe Ala Asn Leu Ile Glu) and five amino acids (Ser Leu Leu Asn Phe). Experimentally produced 4 mm punched wounds on the back of the mice were treated with the ten amino acid version of synthetic Oxynor peptide. The results showed complete closure of the wounds after six days, while the wounds of controls remained open. The histological examination of the skin around the wounds showed epidermis almost like normal skin.

13 Claims, No Drawings

SYNTHETIC PEPTIDE AND USES FOR SAME

This application is a 371 of PCT/US02/02633 filed Jan. 30, 2002 which claims the benefit of provisional application No. 60/264,984 filed Jan. 30, 2001.

TECHNICAL FIELD

The invention relates to a synthetic peptide having mitogenic properties.

BACKGROUND ART

In 1997, the US Food and Drug Administration approved for sale the first recombinant human platelet-derived growth factor (rhPDGF) for treatment of human non-healing wounds. The product is marketed by Ortho-McNeil pharmaceutical and has been approved for use in ulcers of lower-extremity diabetic neuropathy by application of a gel vehicle to promote granulation of wound bed. However, the FDA-approved rhPDGF showed only a 10% efficacy for the patients. There appears to be much room left for improvement.

The venom of the Australian taipan snake, *Oxyuranus s. scutellatus*, contains taipoxin, an abundantly lethal neurotoxin, which has a component, β-taipoxin, which has mitogenic properties. (The intact complex molecule of taipoxin has a molecular weight 45.6 kDa and is composed of alpha (α), beta (β) and gamma (γ) subunits.) Lind reported that the amino acid sequence of the β-taipoxin subunit consisted of 118 amino acids (Lind, P. and Eaker D. (1982). Amino-acid sequence of the β1 Isosubunit of Taipoxin, an Extremely Potent Presynaptic Neurotoxin from the Australian snake Taipan (*Oxyuranus s. scutellatus*). Eur. J. Biochem. 124: 441–443). Lipps reports a partial amino sequence for beta taipoxin and reports that it has utility to promote cell growth in vitro and in the treatment of wounds. (Lipps, B. V., "Beta Taipoxin As A Cell Growth Factor and Method" published PCT application number WO 95/29987, 9 Nov. 1995; see also Lipps, B. V. (2000) "Isolation of subunits, α, β and γ of the complex taipoxin from the venom of Australian taipan snake (*Oxyuranus s. scutellatus*): characterization of β-taipoxin as a potent mitogen.

Toxicon 38: 1–11). However, for a number of reasons, it may prove not to be commercially viable to use taipan snake venom as a natural source for a wound healing product.

It is an object of this invention to provide a peptide which mimics the neurotrophic, keratinocytic and wound healing properties of β-taipoxin, but which is synthetic, rather than derived from venom.

It is another object of the invention is to provide a synthetic peptide which is short enough to be made in cost-effective abundance to provide a highly effective therapeutic for healing wounds and burns and a highly effective growth promoter for the growth of eukaryotic cells in serum-free medium.

It is a further object to provide a treatment for wounds (traumatic, internal, superficial, decubitus ulcers, burns, etc.) by suitable administration of a synthetic peptide to wound area.

DISCLOSURE OF INVENTION

We have discovered a peptide which exhibits wound healing properties. The peptide contains at least a three amino acid portion of the amino acid sequence Lys Gly Gly Ser Leu Leu Asn Phe Ala Asn Leu Ile Glu Asn Asp Val Pro Ile Asp His Met (SEQ ID NO: 1) and no more than 21 amino acids total. The peptide is short enough to be synthesized efficiently and without derivation from snake venom. Fluids containing the peptide are useful for treating wounds and burns, for growing eukaryotic cells in a serum-free medium, and for personal beautification.

BEST MODE FOR CARRYING OUT THE INVENTION

Purification of natural β-taipoxin from Taipan Snake Venom: The homogeneous preparation of β-taipoxin was obtained by fractionating venom on High Performance Liquid Chromatograph (HPLC) using ion exchange column and gradient Trizma buffer pH 7.4. (Lipps (1995) supra).

Trypsin Digestion of natural β-taipoxin: Purified homogeneous preparation of β-taipoxin was treated with trypsin dissolved in 0.1 M ammonium bicarbonate buffer, pH 8.0. The β-taipoxin protein and the trypsin were mixed in a 40:1 ratio. The mixture was incubated at 37° C. to cause fragmentation at arginine and lysine sites. After 18 hours of incubation the reaction was stopped by cooling the mixture at 4° C.

Separation of Fragments from Trypsin Digest: The fragments of β taipoxin digested with trypsin were separated on HPLC. The fragments were collected individually and dialyzed against water using a 500-Dalton molecular weight cutoff tubing (Spectrum USA). The protein concentration of each fragment was measured by spectrophotometer using a protein kit from Bio-Rad. Each fragment was adjusted in concentration to 100 μg/ml with 0.05 M phosphate buffered saline (PBS).

Biological Activity of Fragments on PC12 cells: The trypsin digested fragments in various concentrations were tested for neurite growth on PC12 cells. Tissue culture plates having 24 wells were seeded with $10^5$ PC12 cells in serum free Dulbecco Modified Eagle's medium (DMEM). The results were read after 96 hours for neurite outgrowth.

Identification of Active Fragment

The fragment showing the most neurite growth at the lowest concentration was sequenced by the Protein Core Laboratory of Baylor College of Medicine, Houston, Tex. and found to contain 21 amino acids. The sequence from the N-terminal was determined to be: Lys Gly Gly Ser Leu Leu Asn Phe Ala Asn Leu Ile Glu Asn Asp Val Pro lie Asp His Met (K G G S L L N F A N L I E N D V P I D H M) (SEP ID NO: 1).

Identification of Active Domain

Several synthetic constructs were made based on portions of this sequence by deleting one amino acid from one terminal at a time. In this manner, several constructs consisting of 5 to 21 amino acids were made and tested for mitogenic activity. Of the tested peptides, the 10-amino acid peptide having the sequence from the N-terminal of: Ser Leu Leu Asn Phe Ala Asn Leu Ile Glu (S L L N F A N L I E) (SEQ ID NO: 2) proved to be most active under the conditions of the test. The construct consisting of five amino acids,: Ser Leu Leu Asn Phe (S L L N F) (SEO ID NO: 3) was also found to be active, but less active in comparison to the peptide consisting often amino acids under the conditions of the test. Therefore, the peptide consisting often amino acids from N-terminal having sequence S L L N F A N L I E was selected for further tests. This peptide is designated hereinafter as Oxynor peptide -10.

Biological and Immunological Properties of Oxynor Peptide-10

Incorporation of 2 to 5 82 g/ml of Oxynor peptide-10 in serum-free medium gave cell growth of various cell lines including Vero, Chang's liver, HEp and most importantly skin cells, which was equivalent to growth in medium containing 10% serum, e.g. fetal bovine serum (FBS). Similar concentrations of Oxynor peptide-10 produced neurite growth on PC12 cells. Earlier research had shown that natural β-taipoxin was mitogenic to these cells at 1 to 2 μg/ml in serum free medium. This proves that Oxynor peptide-10 is a mitogen having neurotrophic and keratinocytic properties much like the natural β-taipoxin.

Experimentally produced 4 mm punched wounds on the back of mice were treated with β taipoxin to compare with Oxynor peptide-10 treatment. The results showed complete closure of the wounds after six days while the wounds of controls treated with PBS were open. The histological examination of the skin around the wounds showed epidermis almost like normal skin.

Natural β-taipoxin and Oxynor peptide-10 were tested against each other in vivo at a concentration of 100 μg/ml in hydrogel vehicle applied once daily to help heal 6 mm ischemic skin wounds in rat. At days 7 and 10 the wounds treated with Oxynor peptide-10 were about 15% smaller in area than the wounds treated with natural β-taipoxin. This demonstrates that Oxynor peptide-10 is at least as efficacious as natural β-taipoxin under the conditions of the test.

Anti-β-taipoxin which had been made in mice reacted immunologically with Oxynor peptide-10. This proves that Oxynor peptide-10 is an integral part of the natural β-taipoxin.

Oxynor peptide is defined as a peptide which exhibits wound healing properties and contains at least a three amino acid portion of the amino acid sequence Lys Gly Gly Ser Leu Leu Asn Phe Ala ASN Leu Ile Glu Asn Asp Val Pro Ile Asp His Met (SEP ID NO: 1) and no more than 21 amino acids total. The Oxynor peptide having the just recited sequence of 21 amino acids is termed Oxynor peptide-21. Preferably, Oxynor peptide contains in the range of from 3 to 18 amino acids and more preferably always contains the amino acid sequence Ser Leu Leu Asn Phe (SEQ ID NO: 3). Distinct peptides containing from 5 to fifteen amino acids which include the sequence Ser Leu Leu Asn Phe (SEP ID NO: 3) have been tested and found effective. Exemplary of these peptides are Ser Leu Leu Asn Phe (Oxynor peptide-5) (SEP ID NO: 3), and Ser Leu Leu Asn Phe Ala Asn Leu Ile Glu (Oxynor peptide-10, which has a molecular weight of 1294 daltons) (SEQ ID NO: 2).

The fragment containing Oxynor peptide-21 was isolated and sequenced using automated equipment from Applied Biosystems, Inc. Automated equipment from Applied Biosystems, Inc. has been used for synthesizing other Oxynor peptides with good results. Solid phase chemistry has been used with good results. After synthesizing the peptide, it was cleaved and purified. Because costs increase with the number of amino acids in the peptide, it is expected that different Oxynor peptides containing different numbers of amino acids may be employed for different purposes.

In use, Oxynor peptide is dissolved or dispersed in a suitable carrier fluid, and is preferably applied in a liquid state or as a dispersion in an ointment. Often, a water based carrier fluid, for example, phosphate buffer saline (PBS), is used.

For wound and burn healing, the concentration of Oxynor peptide in the carrier fluid will generally be in the range of from about 0.1 to about 10,000 micrograms/milliliter, usually in the range of from about 10 to about 2000 micrograms/milliliter, and preferably in the range of from about 50 to about 500 micrograms/miliiliter. When Oxynor peptide is used as a replacement for fetal bovine serum to provide a serum free cell growth medium, a concentration on the order of 1% of the foregoing ranges is suitable.

Based on size of wound or burn, the amount of Oxynor peptide applied to the wound is generally in the range of from about 0.01 to about 10,000 micrograms per square centimeter of wound or burn area, usually in the range of from about 0.1 to about 1000 micrograms per square centimeter of wound or burn area, and preferably in the range of from about 0.1 to about 50 micrograms per square centimeter, based on weight of active ingredient. For topical application, the Oxynor peptide can be applied directly to the wound. For internal wounds, such as post operative wounds, the Oxynor peptide can be applied by injection. Thus, Oxynor peptide can be used to treat external and/or internal wounds and surgical incisions as well as burns.

For wound healing, the treatment with Oxynor peptide is repeated at least once daily for a period of time in the range of from 1 to 100 days, usually from 1 to 10 times daily for a period of time in the range of from 3 to 10 days, or until the wound has sufficiently healed so that the treatment can be discontinued. If desired, the Oxynor peptide can be impregnated into a bandage and kept in contact with the wound during the healing process.

Oxynor peptide can also be used to retain the original color of the hair. For this application, Oxynor peptide in carrier fluid at concentrations and in amounts as stated above can be rubbed onto the scalp once or twice a week to reach the desired color and then as required to maintain the desired color. It is contemplated that Oxynor peptide may also be effective to rejuvenate skin (reverse certain indicia of the aging process) by topical application of compositions as described above to the area of skin to be treated. Generally speaking, for this application, the Oxynor peptide would only be applied a few times weekly, again, at a concentration generally as described above.

The invention claimed is:

1. A peptide which exhibits wound healing properties, said peptide consisting of SEQ ID NO:3 and consecutive amino acid residues taken from SEQ ID NO: 1.

2. A peptide according to claim 1 which contains a sequence comprising consecutive amino acid residues 4 to 21 of SEQ ID NO: 1.

3. A peptide according to claim 1 which contains a sequence comprising consecutive amino acid residues 4 to 18 of SEQ ID NO: 1.

4. A peptide according to claim 1 which contains a sequence comprising consecutive amino acid residues 4 to 15 of SEQ ID NO: 1.

5. A peptide according to claim 1 which contains a sequence comprising consecutive amino acid residues Ser Leu Leu Asn Phe Ala Asn Leu Ile Glu (SEQ ID NO: 2) from SEQ ID NO: 1 wherein said sequence is located at the N-terminal region of said peptide and has total amino acid residues up to 15.

6. A peptide of claim 5 consisting of SEQ ID NO: 2.

7. A peptide which exhibits wound healing properties, said peptide being being selected from the group consisting of SEQ ID NO: 1 and a portion of SEQ ID NO: 1 consisting of consecutive amino acid residues taken from SEQ ID NO: 1 and comprising SEQ ID NO: 3.

8. A medication for treating wounds or burns comprising the peptide of claim 1 in a carrier fluid at a concentration in the range of from 0.1 to 10,000 micrograms/milliliter.

9. A cellular growth medium comprising the peptide of claim 1 in an aqueous serum-free growth medium at a concentration in the range of from 1 to 100,000 nanograms/milliliter.

10. A beautifying agent comprising the peptide of claim 1 in a carrier fluid at a concentration in the range of from about 0.1 to about 10,000 micrograms/milliliter.

11. A method for treating wounds or burns comprising administrating to the wound or burn area in a subject the medication of claim 8 in an amount sufficient to provide from 0.01 to 10,000 micrograms of peptide to each square centimeter of said wound or burn area.

12. A method of claim 11 comprising repeating said administration at least once daily for a period of time in the range of from 1 to 100 days.

13. A method of claim 11 wherein the peptide is administered to the wound or burn area by contacting the wound or burn area with a bandage which comprises the peptide.

* * * * *

SEQUENCE LISTING

<160> NUMBER OF SEQ ID NOS: 3

<210> SEQ ID NO 1
<211> LENGTH: 21
<212> TYPE: PRT
<213> ORGANISM: ARTIFICIAL
<220> FEATURE:
<223> OTHER INFORMATION: ACTIVE FRAGMENT OF ISOLATE FROM
      OXYURANUS S. SCUTELLATUS. SYNTHESIZED OR OBTAINED BY TRYPSIN

```
              -continued

DIGESTION.  FOR ISOLATE, SEE LIND, P. AND EAKER D.  (1982)
      AMINO-ACID SEQUENCE OF THE BETA-1 ISOSUBUNIT OF TAIPOXIN...

<400> SEQUENCE: 1

Lys Gly Gly Ser Leu Leu Asn Phe Ala Asn Leu Ile Glu Asn Asp Val
1               5                   10                  15

Pro Ile Asp His Met
            20

<210> SEQ ID NO 2
<211> LENGTH: 10
<212> TYPE: PRT
<213> ORGANISM: ARTIFICIAL
<220> FEATURE:
<223> OTHER INFORMATION: SYNTHESIZED.  CORRESPONDS TO POSITIONS 4-13
      ABOVE.

<400> SEQUENCE: 2

Ser Leu Leu Asn Phe Ala Asn Leu Ile Glu
1               5                   10

<210> SEQ ID NO 3
<211> LENGTH: 5
<212> TYPE: PRT
<213> ORGANISM: ARTIFICIAL
<220> FEATURE:
<223> OTHER INFORMATION: SYNTHESIZED.  CORRESPONDS TO POSITIONS 4-8
      ABOVE.

<400> SEQUENCE: 3

Ser Leu Leu Asn Phe
1               5
```